United States Patent
Wolf et al.

(10) Patent No.: US 8,919,179 B2
(45) Date of Patent: Dec. 30, 2014

(54) SYSTEM AND METHOD FOR ENHANCING CORROSION RATE DETERMINATION IN PROCESS EQUIPMENT USING A TELESCOPING/ROTATING SENSOR

(71) Applicant: ExxonMobil Research and Engineering Company, Annandale, NJ (US)

(72) Inventors: Henry Alan Wolf, Morristown, NJ (US); Alan M. Schliowitz, Highland Park, NJ (US); Manuel S. Alvarez, Warrenton, VA (US); Anastasios Skoulidas, Bristow, VA (US); David Samuel Deutsch, Beaumont, TX (US); Richard J. Basile, Rockaway, NJ (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 35 days.

(21) Appl. No.: 13/710,599

(22) Filed: Dec. 11, 2012

(65) Prior Publication Data
US 2013/0186168 A1    Jul. 25, 2013

Related U.S. Application Data

(60) Provisional application No. 61/570,483, filed on Dec. 14, 2011.

(51) Int. Cl.
*G01N 17/04*    (2006.01)

(52) U.S. Cl.
CPC .................... *G01N 17/04* (2013.01)

USPC ............... 73/1.01; 73/86; 73/866.5; 73/866

(58) Field of Classification Search
CPC ..... G01N 17/02; G01N 17/04; G01N 17/046; G01N 17/043
USPC ........................................................... 76/86
See application file for complete search history.

(56) References Cited

U.S. PATENT DOCUMENTS

| | | | | |
|---|---|---|---|---|
| 3,049,915 A | * | 8/1962 | Freedman et al. | 73/86 |
| 6,035,704 A | * | 3/2000 | Newman | 73/61.41 |
| 7,089,165 B2 | | 8/2006 | Araki et al. | |
| 7,681,449 B2 | * | 3/2010 | Wolf et al. | 73/579 |
| 7,721,605 B2 | * | 5/2010 | Wolf et al. | 73/579 |

(Continued)

OTHER PUBLICATIONS

K.D. Efird et al., "Correlation of Steel Corrosion in Pipe Flow With Jet Impigement and Rotating Cylinder Tests", Corrosion 49 (1993), pp. 992-1003.*

(Continued)

*Primary Examiner* — Peter Macchiarolo
*Assistant Examiner* — Anthony W Megna Fuentes
(74) *Attorney, Agent, or Firm* — Ronald D. Hantman; Bruce M. Bordelon; Andrew T. Ward

(57) ABSTRACT

A system and method for optimizing the response of a metal loss sensor which is configured in a way that its insertion depth and orientation in the process fluid are adjustable. These adjustments affect local turbulence and thereby enable achieving a desired corrosion rate at the metal loss sensor. Corrosion rate comparison between the metal loss sensor and pressure containment boundary can be measured directly or indirectly by computing wall shear stresses at the sensor and the pressure containment boundary.

8 Claims, 7 Drawing Sheets

Corrosion Sensor Inserted to a Specific Depth into the Process Fluid with Respect to a Pipe Wall using a Flange Mounting

(56) References Cited

U.S. PATENT DOCUMENTS

| | | |
|---|---|---|
| 7,886,624 B1 | 2/2011 | Mayeaux |
| 2005/0183969 A1* | 8/2005 | Luopa et al. ............... 205/775.5 |
| 2011/0067497 A1* | 3/2011 | Grubb et al. .................. 73/623 |

OTHER PUBLICATIONS

International Search Report issued Feb. 6, 2013 in corresponding PCT Application No. PCT/US2012/068900, 4 pp.

Written Opinion issued Feb. 6, 2013 in corresponding PCT Application No. PCT/US2012/068900, 8 pp.

Nesic et al., "Comparison of the Rotating Cylinder and Pipe Flow Tests for Flow-Sensitive Carbon Dioxide Corrosion", Corrosion, vol. 51, No. 10, Oct. 1, 1995.

K.D. Efird et al., "Correlation of Steel Corrosion in Pipe Flow With Jet Impingement and Rotating Cylinder Tests", Corrosion 49 (1993), pp. 992-1003.

* cited by examiner

Corrosion Sensor Inserted to a Specific Depth into the Process Fluid with Respect to a Pipe Wall using a Flange Mounting Figure 1b
Corrosion Probe Position Correlates with Wall Shear Stress
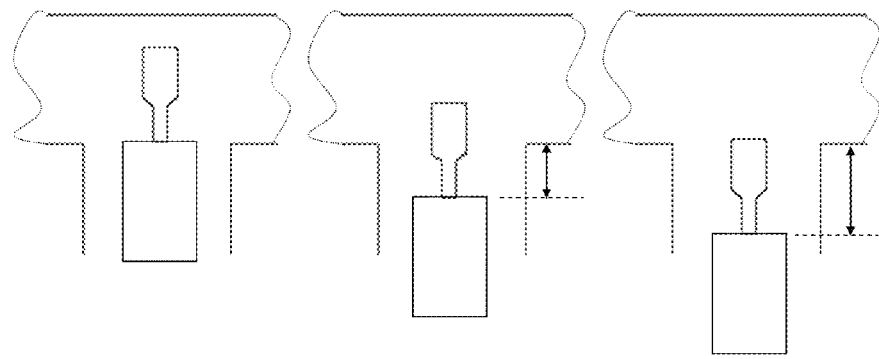
| Insertion Depth (as indicated by the double arrow): | | |
|---|---|---|
| 0 mm | -6 mm | -9 mm |
| Average wall shear stress at corrodible stem | | |
| 147 Pa | 85 Pa | 58 Pa |
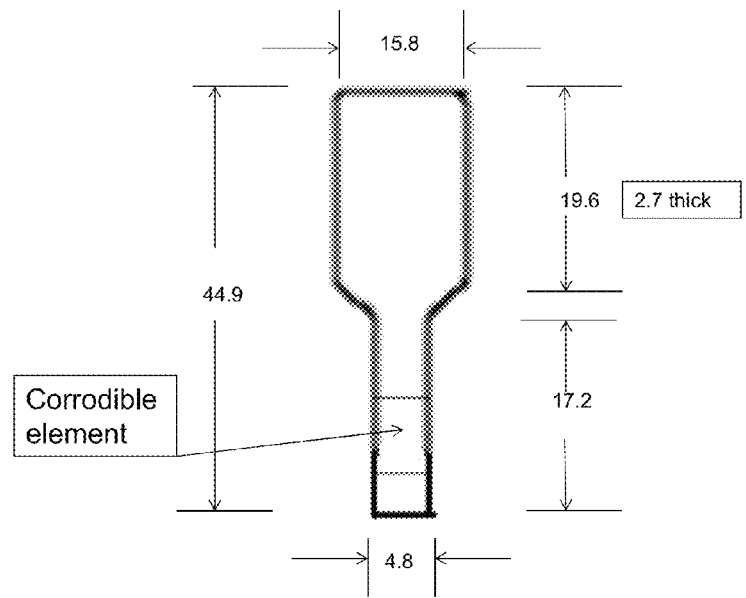
Dimensions are in mm Examples of Wall Shear Stress on Various Piping Components Compared to the Wall Shear Stress at the Corrodible Elements of the Mechanical Oscillator

Figure 3

Flow chart example using pipe geometry: splitting tee

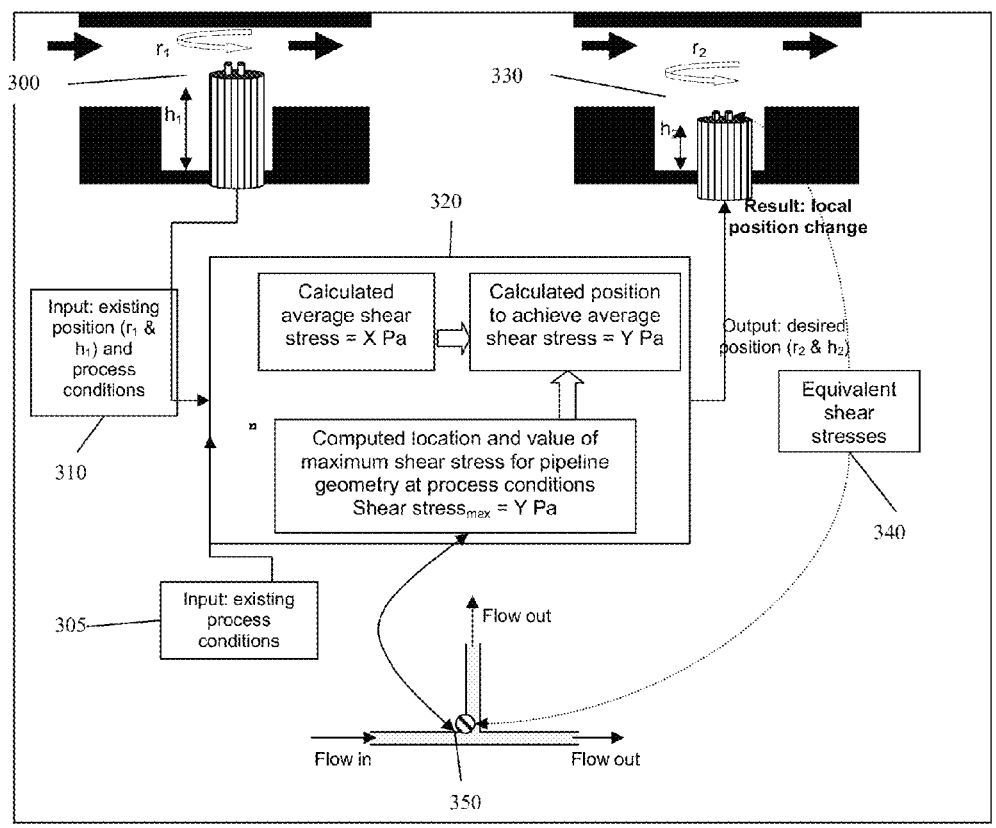

An alternative parameter to wall shear stress is to relate the metal loss sensor response to corrosion rate at the piping component of interest. The corrosion rate can be measured with NDT or with a sacrificial coupon. Once the desired corrosion rate and metal loss sensor relationship is established, the corrosion sensor response can be used to assess metal loss at the remote piping component.

Flow Loop Set-up to Measure and Compare Corrosion at the Metal Loss Corrosion Probes and the Pipe Wall Corrosion Rate Example of probe installation allowing on-stream adjustment of insertion depth Example of Safety Retaining Ring

SYSTEM AND METHOD FOR ENHANCING CORROSION RATE DETERMINATION IN PROCESS EQUIPMENT USING A TELESCOPING/ROTATING SENSOR

FIELD OF THE INVENTION

The present invention generally relates to a system and method for measuring corrosion. In particular, this invention enhances the measurement of corrosion of the process containing vessels and piping of a petroleum unit in a refinery or other industrial process. This enhancement is achieved by the adjustment of the probe alignment and/or insertion depth with respect to the process flow in order to achieve a desired corrosion rate at the probe.

BACKGROUND OF INVENTION

Corrosion is a significant problem in petroleum refineries and other industrial plants which process corrosive materials. Corrosion can cause deterioration of valves, gauges and other process equipment. Corrosion can also cause leaks with large environmental and financial costs.

Various sensors can be used to monitor corrosion. Typically a sensor will be connected to a display which can be monitored to determine the relative corrosion rate which has occurred.

Alternatively, models can be used to predict the level of corrosion from known plant operating parameters. For example, predictive corrosion models exist for estimating corrosion levels from operating temperature, flow conditions and composition of the liquid inside the plant operating unit.

Based on either a sensor or a corrosion model the plant operator can take action if the corrosion rate has reached an excessive level. For example, the operator might choose to reduce throughput, change process conditions, or shut down the process.

Typically, corrosion sensors are fabricated out of a corroding material and corrosion is monitored by measuring the amount of corrosion or corrosion rate which has occurred on the sensor itself. However, one really wants to know how much corrosion has occurred on the equipment being monitored. For example, in the case of a pipe or reactor vessel, one might want to know the corrosion rate or how much corrosion has occurred on the wall of the pipe or reactor vessel, also referred to as the pressure containment boundary.

In some cases, corrosion sensors measure the relative amount of corrosion that has occurred. For example, a corrosion sensor might be able to determine that the corrosion rate has increased. However, it is even more preferable to know the absolute level of corrosion or corrosion rate that has occurred to a process unit—for example on a pipe wall (the pressure containment boundary).

The present invention describes a system and method for adjusting the metal loss rate of a corrosion probe sensor. The adjustment can typically provide a sensitivity increase or decrease compared to the corrosion rate at the vessel pressure containment boundary. In an embodiment where the probe is installed in a straight piping section, it may be desirable to match the corrosion rate with the corrosion rate on an adjacent pipe wall. Alternatively, there may be cases where it is desired to make the measurement in a straight piping section but the desired response is to reflect the corrosion in a potentially more aggressive flow pattern such as in the vicinity of an elbow. The mechanisms and methodology of this invention enable an adjustment to the corrosion probe metal loss rate to accommodate that requirement. This adjustment is made by changing the position (orientation and/or insertion depth) of the probe in the process equipment with respect to the flow. In yet other high corrosion environments, it may be desirable to preserve probe longevity by making adjustments to reduce its corrosion rate.

SUMMARY OF INVENTION

The present invention provides a means for adjusting the metal loss rate of a corrosion probe in accord with flow parameters such as turbulence and wall shear stress. It can be applied to piping or process units in various industries such as refining, chemicals, pulp and paper, and power generation. Examples of units in the refining sector include: pipestills, vacuum pipestills, deasphalters, solvent extractors, hydrocrackers, catalytic crackers, visbreakers, cokers, hydrofiners, reformers, hydrofiners, hydrotreaters, and alkylation units. The method depends on positioning the probe to adjust flow parameters that impact corrosion on the probe such as the wall shear stress or turbulence.

Positioning methods include both probe rotation and depth of insertion into the flow stream. Depending on probe geometry and the insertion mechanism, either or both positioning methods may be used.

It will often be desired to match the corrosion rate at the corrosion sensor to the corrosion rate at other critical locations in the piping fluid flow circuit. In this context, the components in a piping circuit are exposed to a process environment having similar corrosivity as might be considered in the API 570 Piping Inspection Code. Locations of discontinuities in the flow may be associated with high corrosion rates. Examples of such locations include: thermowells, elbows, tees, tower trays, reducers, and expanders.

Several methods are available to match or relate the corrosion rate at the corrosion sensor to the corrosion rate occurring at the remote location in the piping circuit of interest. Example methods include: a) modeling such as computational fluid dynamic (CFD) to assess wall shear stress; b) nondestructive testing methods such as radiography or ultrasonics; c) direct measure of the corrosion rate at the pipe wall compared to the metal loss sensor; or d) multiple corrosion probe sensors. For example, if it were desired to assess the corrosion downstream of an elbow but the corrosion probe were installed in a straight section of a pipe, CFD could be used to calculate the wall shear stress at both locations. With that information, the depth and rotation parameters of the probe in the straight section could be manipulated to achieve the same wall shear stress on the corrosive element of the probe as experienced at the elbow. As subsequently shown, matching wall shear stresses is a first order method of matching corrosion rates for cases where all other chemical and physical parameters are the same. Similarly, nondestructive testing and direct measurement methods, such as corrosion coupons, are also viable for comparing the corrosion rates at the probe and at other locations on the pressure containment boundary. The final case listed above to assess the corrosion rate using multiple corrosion probes is not considered further since one objective of this invention is to minimize the need for using multiple corrosion probes to assess corrosion at several locations in the piping circuit.

In a preferred embodiment, the corrosion sensor is the mechanical oscillator disclosed in U.S. Pat. No. 7,681,449.

BRIEF DESCRIPTION OF THE DRAWINGS

FIG. 1b shows the wall shear stress computed by CFD at the corrosion sensor for three insertion depths FIG. 2 compares the wall shear stress for the FIG. 1b insertions to common pipe geometries where the flow conditions are otherwise identical to the conditions used to compute the wall shear stresses of FIG. 1b.

FIG. 3 presents a flow chart for using the wall shear CFD computation to select the desired probe insertion depth and/or rotation parameters.

DESCRIPTION OF THE PREFERRED EMBODIMENT

The present invention relates the corrosion of a metal loss sensor to the corrosion on the wall of a refinery process unit due to the corrosive fluid inside the unit. More preferably, the metal loss sensor will be similar to the mechanical oscillator described in U.S. Pat. No. 7,681,449. In one preferred embodiment, the corrosion relationship is made by utilizing computational fluid dynamics (CFD) modeling to assess and compare the wall shear stress of the corrosion sensor to the wall shear stress at a remote section at the pressure containment boundary in the piping circuit. In another preferred embodiment, various forms of nondestructive testing (NDT) can be used to establish the corrosion relationship between the corrosion at the probe and the corrosion at the remote location. In another preferred embodiment, a direct measure of corrosion rates at the probe and at the pressure boundary can be employed to establish the necessary relationship. A corrosion coupon can be used to make the direct measurement of corrosion rate.

Figure 1A:
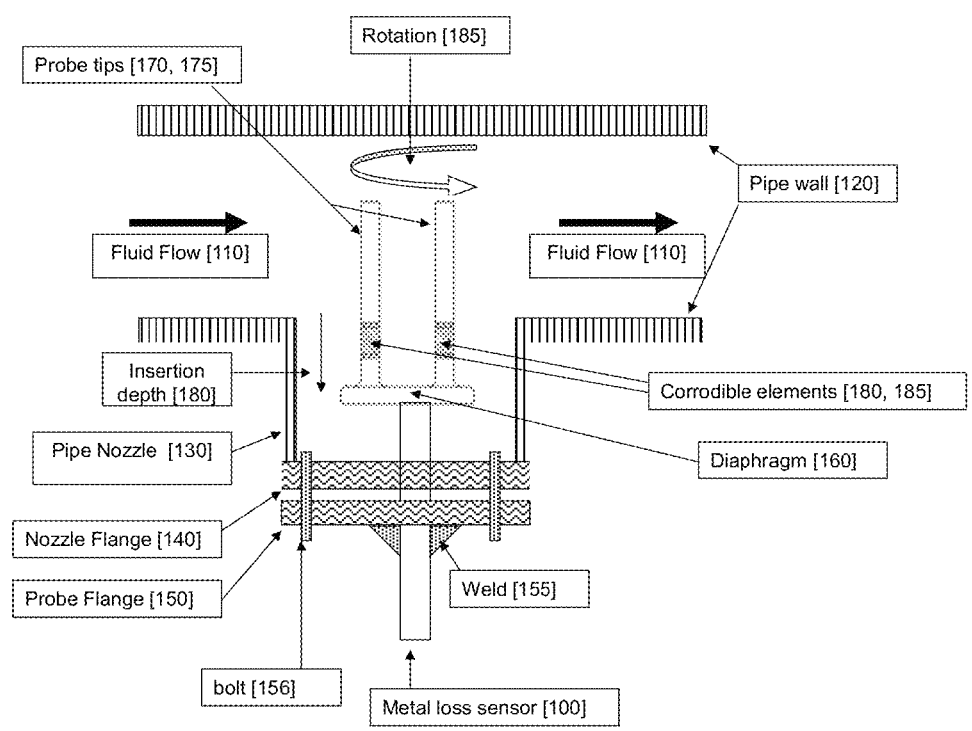
FIG. 1a illustrates a mechanical oscillator corrosion sensor inserted to a specific depth into the process fluid with respect to a pipe wall using a flange mounting.

FIG. 1a shows an example of a metal loss sensor 100 inserted into a fluid flow 110 contained by a pipe 120. The probe is actually inserted through a piping nozzle 130 which is attached to pipe 120. The free end of the piping nozzle has flange 140 which connects to a probe mating flange 150 using bolts 156. The probe 100 and its flange 150 are attached to each other by weld 155. The metal loss sensor in this example has non-corroding elements including a diaphragm 160 and tips 170, 175. The corroding stems 180, 185, are fabricated from the same metallurgy as the pipe wall pressure containment boundary 120. Details of the electrical connections to the sensor are omitted for clarity and are not relevant for this invention.

Corrosion in pipes due to a flowing medium is a complex phenomenon that involves mass transfer through the boundary layer from and to the flow medium, as well as mass transfer through the developing scale or corrosion products layer at the pipe wall. Correlating corrosion rate with the shear stress at the pipe wall, assumes that the mass transfer at the flowing medium boundary layer is controlled by the prevalent hydrodynamics. It is expected that the exact coefficients of the correlating relationship depend on the mass transfer through the developing scale. In particular, it is expected that at low corrosion rates, the mass transfer through the boundary layer is controlling, while at higher corrosion rates a complex interplay between the mass transfer through the boundary layer and the mass transfer through the developing scale will take place, and the controlling step will depend on the particular chemistry and identity of the developing scale.

Computational fluid dynamics (CFD) can be used to compute the wall shear stress on the probe and adjacent piping or piping at remote locations, Computational fluid dynamics (CFD) has been used to compute the wall shear stress for situations using the tuning mechanical oscillator similar to the one described FIG. 1a. An off-the-shelf CFD model (ANSYS Fluent, 275 Technology Drive, Canonsburg, Pa. 15317) based on the Navier-Stokes equation has been used to simulate the single—phase flow through the pipe and around the probe. The CFD methodology employed has been validated by the vendor for a variety of standard single—phase flow problems. CFD computations require that explicit dimensions and flow parameters be used when calculating wall shear stress. To obtain accurate results, care was taken to sufficiently resolve the surfaces of the probe and the pipe according to the vendor recommendations, Using parameters that are consistent with those found in some refining applications, the following details are used as an example:

Where:
$\rho$=fluid density=500 kg/m$^3$
$\mu$=absolute viscosity=1cP
u=fluid velocity=6 msec
$D_{pipe}$=internal diameter of the pipe=152.4 mm
$DH_{stem}$=diameter of the corrodible stem element=4.8 mm
(FIG. 1b shows more detailed dimensions of the probe)
$L_{pipe}$=downstream distance from the probe where the wall shear stress on the pipe is calculated (up to 8.5 pipe diameters; 271 stem diameters)
Re=Reynolds number as determined at the pipe wall or probe stems
Smooth Surfaces for Pipe and Stems Applying these parameters to the ANSYS Fluent model calculates the wall shear stresses illustrated in FIG. 1b. This fluid flow example and probe dimensions are for illustration purposes but could be generalized for other sizes, shapes, and flow conditions. Each of the 3 cases in FIG. 1b is for a different insertion depth 180 of the corrosion probe with respect to the pipe inside wall 120. For the purpose of this example, the insertion depth is a measure of the distance between the probe diaphragm 160 and the pipe internal wall 120. A negative insertion depth implies that the probe is positioned as shown in the −6 and −9 mm examples of FIG. 1b. A positive insertion depth implies that the probe is positioned further into pipe 120. In this example, the diaphragm to pipe wall distance is used as an example reference distance. Any reference distance to describe the position of the probe with respect to the pipe wall is satisfactory.

Figure 2:
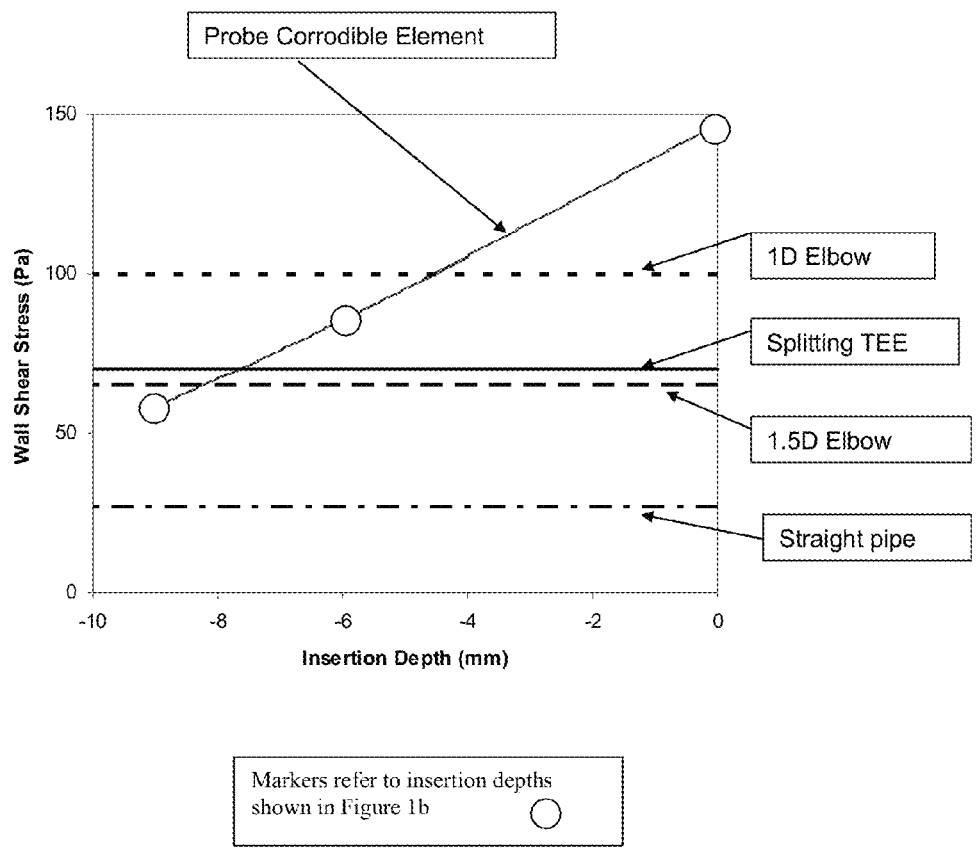

In the FIG. 1b 0 mm case, diaphragm 160 is even with the pipe wall. For the cases labeled −6 mm and −9 mm, the diaphragm is behind the pipe internal wall by those respective amounts. In FIG. 2 it is observed that as more of the stem is immersed behind the pipe wall, the average wall shear stress on the corrodible stems 180, 185 is reduced. Likewise, wall shear stresses on the corrodible stems are increased as the probe is inserted toward the centerline of the pipe (for positive insertion depths).

FIG. 2 plots the average wall shear stress on the corrodible stems 180, 185 as a function of insertion depth. The wall shear stresses for the same flow conditions are shown for 4 common piping components: straight pipe; 1.0D elbow; 1.5D elbow; and a splitting Tee. From the results shown in FIG. 2, it is clear that metal loss sensor insertion depth can be adjusted to achieve a wall shear stress equal to a 1D elbow, a 1.5D elbow, or a splitting TEE. The insertion depth would need to be less than −10 mm to achieve the wall shear stress of straight pipe.

A power-law relationship between corrosion rate and shear stress was developed by Efird, Wright, Boros and Hailey (Efird, K. D.; Wright, E. J.; Boros, J. A.; Hailey, T. G.; "Correlation of Steel Corrosion in Pipe Flow with Jet Impingement and Rotating Cylinder Tests" Corrosion 49 (1993) 992-1003). This relationship is shown by $$R_{corr} = a\tau_w^b \quad \text{Equation 1}$$

In the above equation, $R_{corr}$ is the rate of corrosion in mils/yr and $\tau_w$ is the wall shear stress in N/m², while the coefficient (a) and exponent (b) on $\tau_w$ account for the effects of solution chemistry. For constant process and solution conditions (e.g., temperature, concentration and type of corrosive species, etc.) one can use this equation to compare the corrosion rates of various surfaces. The absolute corrosion rates for each surface can be calculated (using the Equation 1), or relative corrosion rates can be calculated using ratios of the above equation, shown below:

$$R_{corr\ surface\ A}/R_{corr\ surface\ B} = \tau_{wA}^b / \tau_{wB}^b \quad \text{Equation 2}$$

Based on this relationship between corrosion and wall shear stress, it is possible to assess the corrosion rate at other remote but critical locations in the piping circuit using a single metal loss sensor at one location. In this manner, it is possible to relate the corrosion rate of surface B (the pressure containment boundary) as a function of the corrosion rate of surface A (the metal loss sensor) and the respective wall shear stress' at both locations. One approach to optimize the response of the metal loss sensor to corrosion is to select the insertion depth to an amount providing an equivalent wall shear stress at the metal loss sensor and the pressure containment boundary component of interest.

FIG. 3 outlines a flow chart for this approach. In that chart, the FIG. 1 parameters of insertion depth 180 and rotation angle 185 are considered as potential parameters to change the wall shear stress at the metal loss sensor. These insertion parameters are represented by box 300. For cylindrically symmetrical probes, only the insertion depth is available to adjust the wall shear stress at the metal loss sensor. The process conditions as previously enumerated (temperature, flow rate, pipe geometry, fluid density, viscosity) at the proposed probe location are shown as box 305. The probe insertion (depth and rotation) parameters and the process conditions are input at box 310 to the wall shear stress model 320. The wall shear stress model computes the wall shear stress at the probe for the $h_1$ and r values at box 300. Wall shear stress model 320 also computes the wall shear stress to the piping component of interest, 350. For the case in FIG. 3, the objective is to make the wall shear stress at piping component of interest 350 equivalent to the wall shear stress at the probe, as indicated by box 340. The wall shear stress based on $h_1$ and $r_1$, box 300, are compared to the wall shear stress at the piping component of interest, 350. If the two wall shear stress' are not equal, then adjustments of $r_1$ and $h_1$ can be made until they are equal. Once the $r_1$ and $h_1$ adjustments achieve the desired wall shear stress value, that result is noted in box 330 as $r_2$ and $h_2$. The alternative to setting equal shear stress at the metal loss sensor and pressure containment boundary is to use Equation 2 to set a desired or specified corrosion rate offset between the sensor and piping component In some applications it may be satisfactory to use a single metal loss sensor to assess the corrosion situation for an entire piping or process circuit. An example of such a situation would be the case when the locations of maximum corrosion rates are well-anticipated. In some process piping circuits, it may be known that the maximum corrosion rates are associated with turbulent conditions at piping elbows and other areas with high fluid flow turbulence. In many such cases there may be process or access issues that limit or prevent installing the metal loss sensor at those high turbulent locations. With this invention, the metal loss sensor could be installed at an accessible location in a straight piping segment. In one embodiment, wall shear stress is computed at the metal loss sensor and pressure containment boundary high turbulence locations. Those results are substituted into Equation 2 to relate the corrosion at the probe to the corrosion at the more turbulent locations. By selecting the probe insertion depth and orientation with respect to the flow, in accord with FIG. 3, the corrosion at the probe can be matched, enhanced, or attenuated to the corrosion at the remote locations of interest.

Wall shear stress is an example of only one parameter that is available for estimating differences in corrosion rates in a fluid flow circuit. Direct parameters for quantifying differences in corrosion rates are also available. For example, non-destructive testing (NDT) methods (radiographic, ultrasonic, etc. per the ASNT Handbook on Nondestructive Testing) are available for making a direct measure of metal thickness of the piping component. Successive NDT measurements over time at two locations on a piping circuit (a straight section and near an elbow), would establish the corrosion rate difference. Concurrent measurements with the metal loss sensor probe in the straight section would establish the basis for estimating the subsequent corrosion rate at the elbow based on the probe response. A disadvantage of NDT compared to the CFD method is the required time interval for establishing a reliable corrosion rate with NDT metal loss measurements.

Other approaches, such as using a corrosion coupon, are also available to determine the corrosion relationship between the metal loss sensor and the pressure containment boundary. In cases where the piping circuit has provisions for a removable corrosion coupon, weight loss measurements on the corrosion coupon are an alternative to NDT. Successive weight loss measurements of the corrosion coupon will establish the corrosion rate ratio between the corrosion sensor and the coupon.

Figure 4:
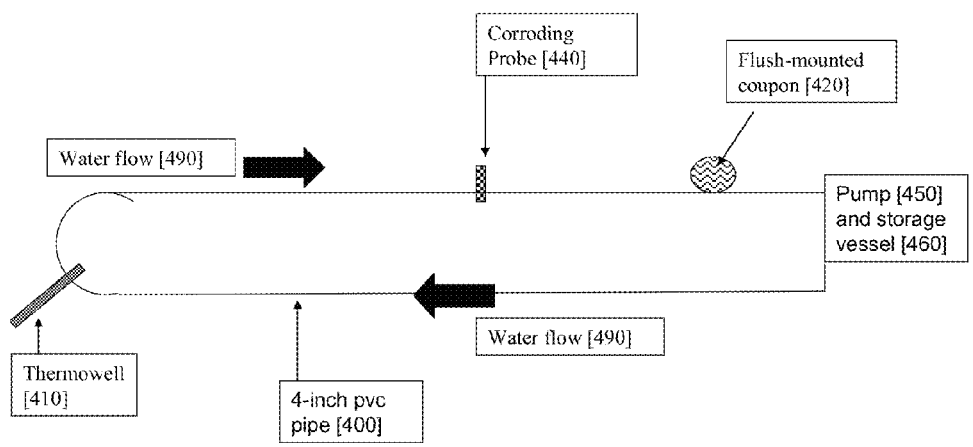
FIG. 4 shows an example flow loop test set-up to directly measure the corrosion rate at the probe and the pressure containment boundary.

Not all piping circuits have provisions for removable corrosion coupons. FIG. 4 shows a flow loop set-up to directly measure the corrosion rate at the probe compared to corrosion rate at the pipe wall using a corrosion coupon. The flow test facility consists of a plastic pipe 400, 4 inches diameter. The overall length of each straight section is approximately 40 feet and the length of the elbow section is approximately 4 feet. The precise construction materials, dimensions, and details are not critical to the practice of the calibration methodology described herein. The facility preferably accommodates at least 1 metal loss coupon 420 that can be removed and weighed as part of the evaluation process. This coupon is mounted flush with respect to the interior of the pipe. The loop shown in FIG. 4 could be modified to include a reference non-corroding reference probe. Corroding probe 440 can be inserted to different depths and rotation angles. Other support components such as a pump and storage vessel 450, 460 are also shown. The FIG. 4 test facility is designed to operate at ambient temperature with water flow 490.

As outlined in FIG. 3, iterative use of the FIG. 4 set-up enables an approach to achieve the desired corrosion ratio between the metal loss sensor and the pressure containment boundary. Flush-mounted metal loss coupon 420 is used to measure the corrosion rate at the pipe wall. For example, if it is desired to match the corrosion rates, a first result from the FIG. 4 set-up may show that the corrosion rate at the sensor is higher than the corrosion rate at the pressure boundary coupon 420. The next test would decrease the insertion depth of the metal loss sensor. Measured corrosion rates using a flow loop, or NDT, or wall shear stress determined CFD are all acceptable parameters for determining the insertion depth. The results from the flow loop set-up are then used to establish the desired corrosion sensor insertion depth and orientation in the piping circuit of interest.

One mounting method of the metal loss sensor to the process piping is with a fixed flange arrangement as shown in FIG. 1. As shown in FIG. 1, flange 150, which is welded 155 to the metal loss sensor 100, connects to nozzle flange 140 which is a part of the process piping 120. In this arrangement, once the flange pair is mated, the probe insertion depth and orientation are fixed.

Figure 5:
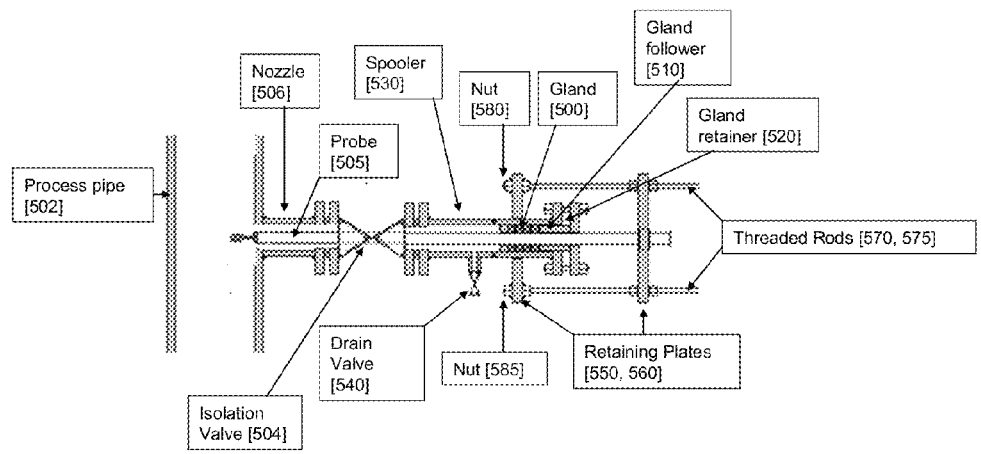
FIG. 5 illustrates a gland mount system for the metal loss sensor enabling on-stream adjustment of insertion depth and rotation angle.

An alternative to the fixed flange mounting of FIG. 1 is the gland mounting assembly shown in FIG. 5. The gland mounting assembly not only enables on-stream adjustment of probe depth, but also enables on-stream retraction or insertion of the metal loss sensor. Similar to the description of FIG. 1, the metal loss sensor 505 shown in FIG. 5 is inserted in the pressure containment boundary or process pipe 502 through nozzle 506. In some cases there may be an optional process isolation valve 504. If the valve 504 is present, it must be of the full port type, enabling the probe to pass through it when the valve is fully open. An advantage of having a process isolation valve is that the probe can be fully removed on-stream. Once the probe is retracted to clear the valve, the valve can be closed and the probe can be fully removed.

The gland mounting assembly contains a pressure containing seal that prevents the passage of process fluid. The seal is made with the gland gaskets 500. The gland follower 510 and follower retainer 520 enable the proper compression to be applied to the gland gaskets 500. Grafoil® is an example of a gland gasket material that is satisfactory at high temperatures for a variety of corrosive environments. An insertion/retraction mechanism is also illustrated in FIG. 5. The insertion/retraction mechanism is operatively connected to the gland mounting assembly. The mechanism includes a spooler section 530 that facilitates probe installation with two features: drain valve 540 and retaining plate 550. Retaining plate 550 is welded to the spooler. There is a corresponding retaining plate 560 welded to probe 505. The two retaining plates are connected by threaded rods 570, 575. Simultaneous screwing of the threaded rods at nuts 580, 585 facilitates probe insertion or extraction. The operation of only one of the threaded rods permits angular adjustment of the metal loss sensor such that angular orientation of the metal loss sensor may be adjusted with respect to the flow of the process fluid. Drain valve 540 enables a means to empty the spooler when process valve 504 is closed.

When a retractable gland mounting arrangement similar to that of FIG. 5 is used, safety issues must be considered that are not relevant for the fixed flange mount approach of FIG. 1. Leakage at the gland is possible if the gland material is not properly seated around the probe. Moreover, there is also a possibility that pressure variations in the process could cause the probe to blow out. Two schemes to prevent blowouts are: 1) a retaining ring near the end of the probe and 2) cabling. Either or both may be used. The retaining ring diameter is slightly smaller than the internal diameter of the nozzle and spooler but it is too large to fit through the gland. Therefore, the probe can only be pulled out up to the gland. The cabling approach secures a taught cable to the probe and to the spooler. The cable is pulled taught and secured once the probe insertion depth has been reached. The cable must be removed or loosened to remove the probe.

Figure 6:
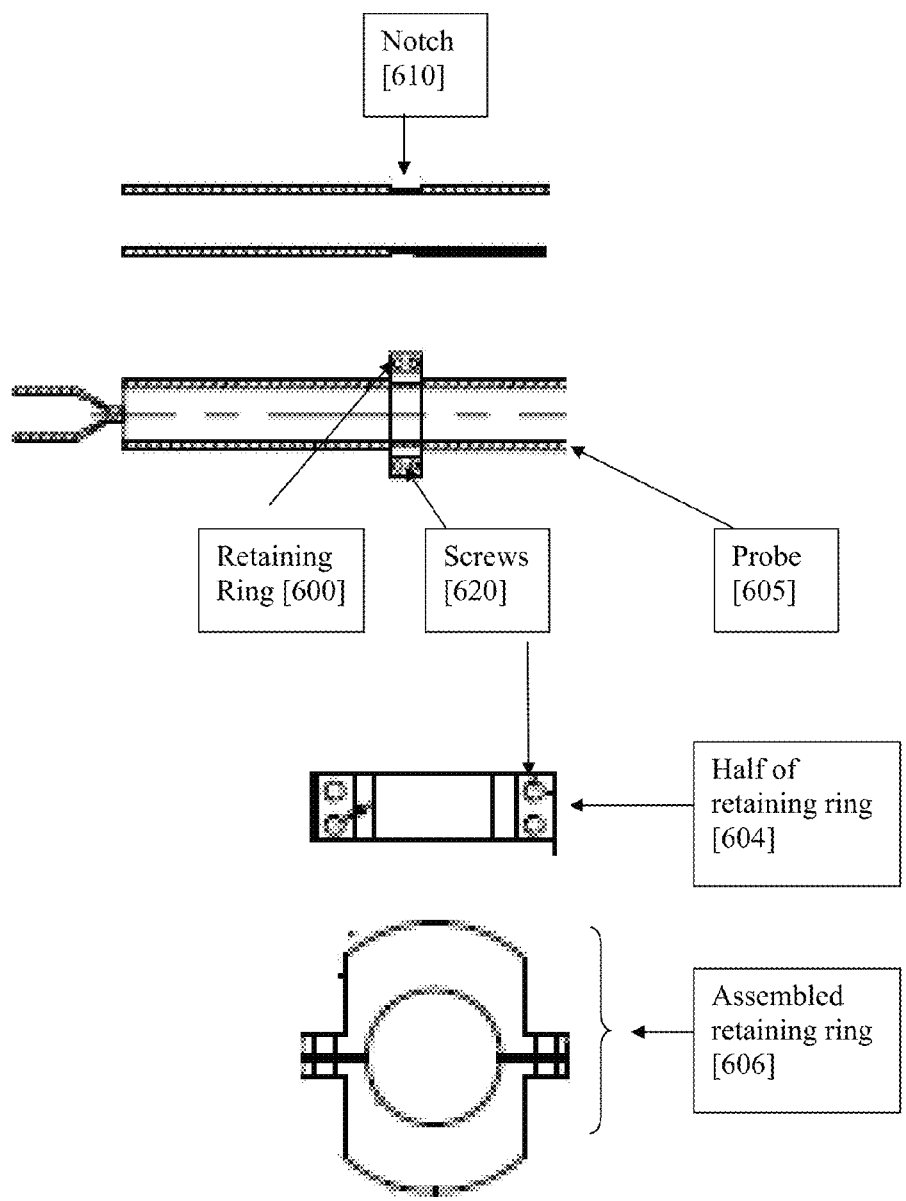
FIG. 6 shows the details of a removable retaining ring to prevent unintentional blowout of a retractable probe.

FIG. 6 presents a design of a removable retaining ring. A removable retaining ring is advantageous compared to a permanently installed, welded in place retainer. In particular, a removable retaining ring enables the probe assembly to be fabricated and shipped to the installation site separately from the full spooler and retraction/insertion assembly. As shown in FIG. 6, one design for the removable retaining ring 600, 606 is to make the ring in two separate halves 604 assembled by screws 620. By machining a notch 610 into probe tube 605, the retaining ring cannot slide.

The insertion/retraction mechanism described in FIG. 5 provides one specific example of a device that enables on-stream adjustment of probe position. Variations should be obvious to one skilled in the art. For example, an alternative to welding retaining plate 560 to the probe is to make the attachment with collars and set screws. That modification enables adjustment of the probe angle as well as the probe depth. An alternative to the gland seal is a bellows.

What is claimed is:

1. A method for adjusting a metal loss rate of a metal loss sensor installed adjacent a pressure containment boundary in one of a piping and a process unit that is exposed to a fluid flow of a corrosive fluid comprising:
   measuring a corrosion rate of the metal loss sensor installed adjacent the pressure containment boundary;
   relating the corrosion rate at the metal loss sensor to the corrosion rate at the pressure containment boundary; and
   adjusting a position of the metal loss sensor with respect to the corrosive fluid to achieve a desired relationship between the corrosion rate at the metal loss sensor and the pressure containment boundary, wherein the adjustment of the metal loss sensor is determined by the relating the corrosion rate at the metal loss sensor to the corrosion rate at the pressure containment boundary.

2. A method for adjusting a metal loss rate of a metal loss sensor installed adjacent a pressure containment boundary in one of a piping and a process unit that is exposed to a fluid flow of a corrosive fluid comprising:
   measuring a corrosion rate of the metal loss sensor installed adjacent the pressure containment boundary;
   relating the corrosion rate at the metal loss sensor to the corrosion rate at the pressure containment boundary, wherein the relating the corrosion rates is accomplished by determining a wall shear stress associated with a flow turbulence; and
   adjusting a position of the metal loss sensor with respect to the corrosive fluid to achieve a desired relationship between the corrosion rate at the metal loss sensor and the pressure containment boundary.

3. The method of claim 1 wherein the relating the corrosion rates is accomplished by a direct measurement of the corrosion rate at the pressure containment boundary.

4. The method of claim 2 wherein the wall shear stress is determined using computational fluid dynamics.

5. The method of claim 3 wherein the direct measurement of the pressure containment boundary is made using nondestructive testing.

6. The method of claim 3 wherein the direct measurement of the pressure containment boundary is made using coupons fixed to the pressure containment boundary.

7. The method according to claim 1, wherein said metal loss sensor is a mechanical oscillator.

8. The method according to claim 1, wherein the fluid flow is stagnant.

* * * * *